United States Patent [19]
Yamada et al.

[11] Patent Number: 6,165,982
[45] Date of Patent: Dec. 26, 2000

[54] USE OF SERICIN AS ANTIOXIDANTS AND TYROSINASE INHIBITORS

[75] Inventors: Hideyuki Yamada, Fukui; Naozumi Fuwa, Fukui-ken; Masakazu Nomura, TaKefu, all of Japan

[73] Assignee: Seiren Co., Ltd., Fukui, Japan

[21] Appl. No.: 08/964,100

[22] Filed: Nov. 6, 1997

[30] Foreign Application Priority Data

Nov. 8, 1996 [JP] Japan .................................... 8-296015
Mar. 24, 1997 [JP] Japan .................................... 9-069416

[51] Int. Cl.⁷ .................................................... A61K 38/00
[52] U.S. Cl. .............................. 514/21; 252/397; 424/70; 426/541
[58] Field of Search ................................. 424/70; 514/21; 252/397; 426/541

[56] References Cited

U.S. PATENT DOCUMENTS 4,839,165   6/1989   Hoppe et al. .............................. 424/70
5,504,228   4/1996   Morelle et al. ........................... 554/69

OTHER PUBLICATIONS

Chem. Abstr., vol. 76, abstr. #23236, 1972.

*Primary Examiner*—Deborah D. Carr
*Attorney, Agent, or Firm*—Dilworth & Barrese, LLP

[57] ABSTRACT

This invention relates to a composition useful as an antioxidant or an inhibitor for tyrosinase activity which comprises as an active ingredient a sufficient amount of sericin to exert an antioxidizing ability or an inhibiting action on tyrosinase activity and this composition is applicable as an antioxidant or a tyrosinase activity inhibitor in the field of medicines, quasi-drugs, medicines for external use, cosmetics, foods, food additives or the like.

15 Claims, No Drawings

USE OF SERICIN AS ANTIOXIDANTS AND TYROSINASE INHIBITORS

FIELD OF THE INVENTION

This invention relates to a novel antioxidant or tyrosinase inhibitor which can be employed in the various fields of, for example foods, cosmetics, medicines and others. More particularly, this invention relates to a novel antioxidant or tyrosinase inhibitor which comprises as an active ingredient sericin, a protein obtainable from silkworm cocoon or raw silk.

BACKGROUND OF THE INVENTION

Recently, it has been suggested from the researches made in the field of medicine, biochemistry and others that adult diseases or diseases caused from daily life habit such as myocardial infarction, arteriosclerosis, diabetes mellitus, cancer, cerebral apoplexy and the like or cutaneous disorders such as blotch, freckle, pimple, eczema and the like may be at least partly caused from the lipid peroxide produced and accumulated in vivo.

In order to solve such problems, there have been hitherto suggested antioxidants obtainable by the extraction of natural products such as plants, marine products, microorganisms and the like or chemically synthesized antioxidants. There have been, for example, utilized as natural antioxidants vitamin E (tocopherol), vitamin C (L-ascorbic acid), or a SOD (superoxide dismutase; one of in vivo enzymes)-like substance. There have been also suggested as synthetic antioxidants phenolic derivatives such as BHA (butyrated hydroxyanisole), BHT (butyrated hydroxytoluene) and the like.

However, in the case of natural antioxidants, for instance, SOD has the drawbacks that it is highly expensive owing to difficulty in purification and may be inactivated by heating owing to an enzymatic protein. Although other antioxidative proteins are also found, they all have the similar drawbacks as seen in the SOD. In regard to synthetic antioxidants, there has been posed the problem on safety and, in particular, BHA has been suspicious of carcinogenicity. Moreover, when used for foods, many of them have been restricted in the amount to be used or the extent of their usage.

Many of natural and synthetic antioxidants are usually fat-soluble and, in the case of natural antioxidants, vitamin E or β-carotene may possess, for example, a potent in vivo inhibitory effect on lipid peroxide, but it has the problem of a restricted usage extent because of a slight solubility in water. Water-soluble natural antioxidants are restricted in their sort and there may be solely mentioned, for example, vitamin C, glutathione, uric acid, SOD, etc.

However, vitamin C and glutathione may act as a pro-oxidant, i.e. an oxidation promoter in the presence of a metallic ion and have the drawback that they tend to promote the peroxidation of lipid under some conditions. Uric acid is water-soluble, but slightly soluble in water and, when accumulated in vivo, it may be responsible for gout or renal calculus.

Moreover, there has been posed the problem that there have been found out few natural water-soluble antioxidants having a high lipid peroxide inhibiting effect comparable to vitamin C.

Tyrosinase is one kind of enzymes having the activity of monophenol monooxygenase EC 1. 14. 18. 1. The enzyme of this type is widely distributed in animals, plants and microorganisms, typically melanocyte, house fly, mushroom, potato, apple, Neurospora, etc. Recently, the enzyme of this type has been highly purified from various materials, and, for example, it is purified from the fruit body of mushroom by acetone treatment, ammonium sulfate fractionation, ion exchange or gel filtration. Its molecular weight is 119,000 in the enzyme derived from mushroom, 144,000 in the enzyme derived from higher plants or 33,000 in the enzyme derived from Neurospora, and its molecular weight may considerably vary depending upon its origin. All of these enzymes are of a copper enzyme, but their copper contents may be different. It is specific to such substrate as monophenol or o-diphenol and, in particular, the enzyme derived from animals shows a high activity to DOPA and deeply participates in the first stage of melanin biosynthesis. This may be expressed according to the following reaction scheme:

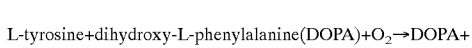

Melanin is a pigment which is distributed in the hair or skin in the case of human beings and responsible for the determination of their coloration. Formation of melanin in the skin is one of human protective functions. Biosynthesis of melanin in animals may proceed as follows: First, when exposed to ultraviolet ray, the tyrosinase in melanosome found in melanocyte is activated and DOPA and DOPA-quinone are in turn biosynthesized as shown in the above reaction scheme. Thereafter, the DOPA-quinone is polycondensed in turn by non-enzymatic oxidation, decarboxylation and coupling reaction to form melanin. When released from irradiation with ultraviolet light, melanin is separated from the corneum by metabolism in the skin to recover the skin coloration. On the other hand, when stimulated, for example, by exposing a high irradiation of ultraviolet light, the melanin-forming function is locally maintained and the corresponding region of the skin remains blackened to cause pigmentation or blotch.

In the field of foods, for example, when the captured crustaceans are dead, the crust of the crustaceans becomes discolored within a short period of time. When fruits and vegetables such as apple, yam or lettuce are peeled or cut, the inner parts thereof are discolored within a shot period of time. This phenomenon is caused from the activation of tyrosinase found in the said crustaceans or fruits and vegetables and subsequent formation of melanin as the reaction product.

In order to prevent such pigmentation or blotch in the skin caused by melanin formation, promote a cosmetic bleaching effect or prevent discoloration of foods, there have been hitherto applied an inhibitory agent for tyrosinase activity to prevent melanin biosynthesis. For example, there have been suggested as a synthetic tyrosinase inhibitor various sulfite salts and as a natural tyrosinase inhibitor kojic acid, placenta extract, vitamin C, cysteine or extracts having an inhibiting function on tyrosinase activity which are derived from plants and the like.

However, there have been proposed some problems of safety to a human body. There is the danger, for instance, that allergic response in a human body may be observed for the sulfites or, when the sulfites are used for crustaceans, formaldehyde may be generated during the storage. Although sodium sulfite or sodium hydrogensulfite is designated as food additives, the criterion for its usage has been specified and its residue in foods has been also regulated.

In the case of natural tyrosinase inhibitors, for instance, kojic acid is difficult to be produced or purified and then becomes expensive. More specifically, a strain capable of producing kojic acid is cultivated, and kojic acid is extracted from cultured broth containing the acid as a main component and then crystallized. On the other hand, it has been observed that some strains capable of producing kojic acid could also produce aflatoxin having a potent carcinogenic activity, which leads to the problem of safety. Placenta extract is also difficult to be produced or purified similarly to the case of kojic acid and expensive, too. In the case of vitamin C, the enzymatic oxidation reaction by tyrosinase (as shown in the above reaction scheme) is controlled by reducing power of the said vitamin itself. Accordingly, ascorbic acid is converted to dehydroascorbic acid and ascorbic acid is decreased with lapse of time so that its inhibitory activity could not be maintained. In the case of cysteine, an inhibitory activity could not be maintained because of cysteine itself being oxidized similarly to the case of vitamin C and it has the drawback that it may be discolored to black as oxidized. Extracts derived from plants and others by extraction and having an inhibiting function on tyrosinase activity are difficult to be identified for their chemical composition with a low purity. In addition, there is the possibility that quality of the extract may be variable in lot-to-lot.

Moreover, most of the prior art tyrosinase activity inhibitors are fat-soluble and the water-soluble inhibitors for tyrosinase activity are limited in availability.

SUMMARY OF THE INVENTION

It is an object of this invention to provide a composition having a high antioxidizing activity and a high inhibiting action on tyrosinase activity, which has a high safety because of originating from natural products, is not deactivated even by heating, can be easily and inexpensively produced or purified and is water-soluble in a single, high purity.

According to this invention, there is provided a composition useful as an antioxidant and a tyrosinase activity inhibitor which comprises as an active ingredient a sufficient amount of sericin to exert an antioxidizing ability and an inhibiting action on tyrosinase activity.

DETAILED DESCRIPTION OF THE INVENTION

As the sericin which may be employed in this invention, there may be preferably used sericin which has a high purity and is usually derived from silkworm cocoon or raw silk and includes its hydrolyzate.

The sericin hydrolyzate which may be employed in this invention may be obtained from silkworm cocoon or raw silk according to a conventional extraction method. For instance, it may be extracted in the form of a single protein with a 90% or higher purity according to the following procedure.

That is to say, the sericin contained in silkworm cocoon or raw silk is extracted with water and then subjected to, for example, the following procedure (1), (2) or (3) to give a sericin.

Alternatively, the sericin hydrolyzate which may be employed in this invention may be obtained from silkworm cocoon or raw silk according to a conventional extraction method. For instance, it may be extracted in the form of a single protein (a peptide) with a 90% or higher purity according to the following procedure.

That is to say, the sericin contained in silkworm cocoon or raw silk is extracted and partially hydrolyzed with an acid, an alkali or an enzyme and then subjected to, for example, the following procedure (1), (2) or (3) to give a sericin hydrolyzate.

(1) An aqueous solution of sericin is adjusted to pH 3~5 with an organic acid or an inorganic acid, an organic coagulating agent or an inorganic coagulating agent to separate out sericin, which is then filtered and dried to give a solid sericin.

(2) An aqueous solution of sericin is admixed with a water-miscible solvent such as methanol, ethanol or dioxane to separate out sericin, which is then filtered and dried to give a solid sericin.

(3) An aqueous solution of sericin is passed through a dialysis membrane to remove the substance passed through the membrane and then the substance left on the membrane is dried to give a solid sericin.

The free sericin base or sericin hydrolyzate obtained as described above may be used in any suitable form, for example, in the form of its solid as it stands or in the form of a solution dissolved in a solvent, preferably an aqueous solution dissolved in a proper volume of water, in compliance with the intended use as an antioxidant or a tyrosinase activity inhibitor.

The sericin or its hydrolyzate may be utilized for cosmetics, foods, food additives, medicines for external use, quasi-drugs, medicines, etc. similarly to the antioxidants or tyrosinase activity inhibitors of the prior art.

An amount of the sericin to be blended is usually about 0.1~50% by weight, preferably about 0.5~5% by weight, for example, in cosmetics, food additives, medicines for external use, quasi-drugs and the like. An amount of the sericin to be blended is usually about 0.1~100% by weight preferably about 0.5~50% by weight in foods. As sericin has no toxicity and a superior solubility in water, there would not be posed any specific problem even if a large amount thereof may be blended or taken.

A dosage form of cosmetics or medicines for external use may include, for example, creams, emulsions, foundations, packs, lotions, gel-, solution- or stick-like dosage forms and the like. These dosage forms may be optionally blended with any suitable components conventionally used in the corresponding fields, such as lubricants, humectants, thickening agents, preservatives, emulsifying agents, pigments, pH adjustors, other active components, ultraviolet absorbers, perfumes, etc.

The sericin or its hydrolyzate may be orally administered as medicines. In this instance, a dose is not particularly critical and it may be administered, for example, at a dose of about 10 mg~100 g/day.

As an alternative embodiment of this invention, there may be concomitantly used with sericin or its hydrolyzate in the composition of this invention any other active components or additive components which are conventionally added to the prior art antioxidants or tyrosinase activity inhibitors. These components are not particularly critical and may be optionally incorporated, in addition to the main active ingredient, i.e., sericin or its hydrolyzate.

Representative examples of these components which may be concomitantly employed in the field of foods for the favorable results will be recited hereinbelow.

Discoloration inhibitors: Polyphosphoric acid or salts thereof, metaphosphoric acid or salts thereof, pyrophosphoric acid or salts thereof, citric acid or salts thereof, potassium aluminum sulfate, erythorbic acid or salts thereof and the like.

Antimicrobial agents and preservatives: benzoic acid or salts thereof, orthophenylphenol or salts thereof, diphenyl, sorbic acid or salts thereof, thiabendazole, dehydroacetic acid or salts thereof, paraoxybenzoic acid alkyl esters, propionic acid or salts thereof, bleaching powder, hypochlorous acid or salts thereof, fumaric acid, ε-polylysine, glycine, lysozyme, anise extract and the like.

Representative examples of these components which may be concomitantly employed in the field of cosmetics for the favorable results will be recited hereinbelow.

Astringents: citric acid or salts thereof, tartaric acid or salts thereof, lactic acid or salts thereof, aluminum chloride, potassium aluminum sulfate and the like.

Antimicrobial agents and preservatives Benzoic acid, sodium benzoate, paraoxybenzoic acid esters, distearylmethylammonium chloride, benzethonium chloride, alkyldiaminoethylglycine chloride solutions, chlorhexidine dihydrochloride, orthophenylphenol, sensitizing dye No. 101, sensitizing dye No. 201, salicylic acid, sodium salicylate, sorbic acid, halocarban, resorcin, parachlorophenol, phenoxyethanol and the like.

Cosmetic bleaching agents: Ascorbic acid and derivatives thereof, sulfur, placenta extract, kojic acid and derivatives thereof, glucosamine and derivatives thereof, azelaic acid and derivatives thereof, arbutin and derivatives thereof, hydroxycinnamic acid and derivatives thereof, glutathione and the like.

Ultraviolet absorbers: β-Isopropylfuranone derivatives, urocanic acid, ethyl urocanate, oxybenzone, oxybenzone-sulfonic acid, tetrahydrobenzophenone, dihydroxydimethoxybenzophenone and the like.

Humectants Glycine, threonine, alanine, collagen, hydrolyzed collagen, vitronectin, fibronectin, keratin, elastin, royal jelly, chondroitin heparin and the like.

Cell activators Riboflavin or derivatives thereof, pyridoxine or derivatives thereof, nicotinic acid or derivatives thereof, pantothenic acid or derivatives thereof.

Anti-inflammatory agents and anti-allergic agents: azulene, allantoin, aminocaproic acid, indomethacin, lysozyme hydrochloride, ε-aminocaproic acid the like.

Fats and oils soybean oil, linseed oil, tung oil, sesame oil and the like.

Hydrocarbons: Liquid paraffin, Vaseline, microcrystalline wax and the like.

Aliphatic acids: stearic acid, linoleic acid, lauric acid, myristic acid, palmitic acid and the like.

Alcohlols: Lauryl alcohol, cetyl alcohol, stearyl alcohol, lanolin alcohol, hydrogenated lanolin alcohol, oleyl alcohol and the like.

Esters Decyl oleate, butyl stearate, myristyl myristate, hexyl laurate, isopropyl palmitate and the like.

Surfactants Anionic surfactants, cationic surfactants, amphoteric surfactants, nonionic surfactants.

Perfumes: Menthol, carvone, eugenol, anethole, peppermint oil, spearmint oil and the like.

DESCRIPTION OF SPECIFIC EMBODIMENTS

EXAMPLE 1

1 kg of silk cloth composed of raw silk was treated in 50 L of water at 95° C. for 2 hours to extract sericin. The resulting extract was filtered through a filter having an average pore diameter of 0.2 μm, the aggregate was removed and the filtrate was desalted through a reverse osmotic membrane to afford a colorless, clear solution of sericin in water with a concentration of 0.2%. This aqueous solution was concentrated by means of an evaporator to a sericin concentration of about 2% and then freeze-dried to afford 100 g of a powdery sericin (hereinafter referred to as Sericin H) having a purity of 95% or higher and an average molecular weight of 100,000.

EXAMPLE 2

1 kg of silk cloth composed of raw silk was treated in 50 L of a 0.2% aqueous solution of sodium carbonate (pH 11~12) at 95° C. for 2 hours to extract a sericin hydrolyzate. The resulting extract was filtered through a filter having an average pore diameter of 0.2 μm, the aggregate was removed and the filtrate was desalted through a reverse osmotic membrane to afford a colorless, clear solution of a sericin hydrolyzate in water with a concentration of 0.2%. This extract was concentrated by means of an evaporator to a sericin concentration of about 2% and then freeze-dried to afford 100 g of a powdery sericin hydrolyzate (hereinafter referred to as Sericin L) having a purity of 90% or higher and an average molecular weight of 20,000.

TEST EXAMPLE 1

(1) Preparation of rat brain homogenate

To 1 g of the rat brain stored under refrigeration was added 9 ml of 0.075M phosphate buffer (pH 7.5) and the mixture was homogenated under ice-cooling (hereinafter referred to as homogenate).

(2) Inhibitory test of in vivo lipid peroxide

To 0.5 ml of the homogenate obtained above was added 3.5 ml each of 0.075M phosphate buffers containing Sericin L and Sericin H (pH 7.5), respectively. Incubation was continued at 37° C. for 2 hours. At the end of this time, the respective final concentrations of sericin were made to 0.02~0.5%. Immediately before the isolation and after the incubation for 2 hours, 0.5 ml each of the samples was recovered and then TBARS (thiobarbituric acid reactive substance), an indicator of lipid peroxide level, was determined according to the TBA (thiobarbituric acid) method. Antioxidizing ability of sericin was calculated from the TBARS amount obtained when no sericin was added and the TBARS amount obtained when sericin was added according to the following equation 1 and expressed in terms of an inhibitory rate on an increase in lipid peroxide by incubation. In all cases of this Test Example and the following Test Examples 2~5, tests were repeated three times and the results were shown with an average value of the numerical values thus obtained.

$$\text{Inhibitory rate } (\%) = (1 - A/B) \times 100 \qquad \text{Equation 1}$$

A: Increased TBARS amount obtained when a lipid peroxide inhibitory agent (an antioxidant) was added B: Increased TBARS amount obtained when no lipid peroxide inhibitory agent (an antioxidant) was added TBA method To 0.5 ml of a sample were added 2.5 ml of a 8% trichloroacetic acid solution and 2.0 ml of a 0.67% thiobarbituric acid solution and the resulting mixture was thoroughly mixed and then heated in a boiling water bath for 15 minutes. Thereafter, the mixture was centrifuged at 2000× g for 10 minutes and the supernatant was measured for absorbance at 535 nm to determine a TBARS amount. 1,1,3,3-Tetraethoxypropane was used as a standard.

TABLE 1

| Concentration(%) | Inhibitory rate(%) | |
|---|---|---|
| | Sericin L | Sericin H |
| 0.02 | 9 | 12 |
| 0.05 | 18 | 27 |
| 0.1 | 55 | 20 |
| 0.3 | 100 | 54 |
| 0.5 | 95 | 95 |

As shown in Table 1, it has been established that both Sericin L and Sericin H possess an antioxidizing ability. It has been established that a sericin having any molecular weight may possess an antioxidizing ability.

TEST EXAMPLE 2

(1) Preparation of rat brain homogenate

Preparation was carried out in the same man as described in Test Example 1.

(2) Inhibitory test of in vivo lipid peroxide

To 0.5 ml of the homogenate obtained above was added 3.5 ml each of 0.075M phosphate buffers (pH 7.5) containing Sericin L, ascorbic acid (vitamin C) and bovine serum albumin, respectively. Incubation was continued at 37° C. for 2 hours. The final concentrations of Sericin L, ascorbic acid and albumin were made to 0.01%~1.0%. After incubation, a TBARS amount was determined according to the TBA method, similarly to Test Example 1 and inhibitory rates on an increase in lipid peroxide were determined, respectively.

TABLE 2

| Concentration(%) | Sericin L | Ascorbic acid | Albumin |
|---|---|---|---|
| 0.01 | 3 | −39 | −6 |
| 0.05 | 13 | 39 | −4 |
| 0.1 | 86 | 87 | −12 |
| 0.5 | 96 | 97 | 20 |
| 1.0 | 97 | 96 | 30 |

As shown in Table 2, it has been confirmed that a level of an antioxidizing ability of sericin is comparable to that of vitamin C which has been said to have a potent antioxidizing ability. Moreover, it was found the drawback in the case of vitamin C that oxidation may be accelerated in a low concentration range of 0.01%, whereas such a phenomenon was not observed in the case of sericin.

TEST EXAMPLE 3

(1) Preparation of rat brain homogenate

Preparation was carried out in the same manner as described in Test Example 1.

(2) Inhibitory test of in vivo lipid peroxide

To 0.5 ml of the homogenate obtained above was added 3.5 ml each of 0.075M phosphate buffers containing Sericin L and Sericin H (pH 7.5), respectively. Incubation was continued at 37C for 2 hours. Separately, to 0.5 ml of the homogenate obtained above was added 3.5 ml of 0.075M phosphate buffers containing Sericin L and Sericin H (pH 7.5), which had been previously heated in a boiling water bath for 2 hours, and incubation was continued at 37° C. for 2 hours. At the end of this time, the final concentration of sericin was made to 0.5%. A TBARS amount was determined according to the TBA method, similarly to Test Example 1, an inhibitory rate on an increase in lipid peroxide was determined.

TABLE 3

| | Inhibitory rate(%) |
|---|---|
| 0.5% Unheated Sericin L | 99 |
| 0.5% Heated Sericin L | 99 |
| 0.5% Unheated Sericin H | 85 |
| 0.5% Heated Sericin H | 78 |

Even when Sericin L or Sericin H was heated in a boiling water bath for 2 hours and an antioxidizing ability was determined, there was hardly seen a change between said antioxidizing ability and the antioxidizing ability before heating. It has been proved from the results that an antioxidizing ability of sericin could not be inactivated by heating.

TEST EXAMPLE 4

(1) Preparation of rat brain homogenate

Preparation was carried out in the same manner as described in Test Example 1.

(2) Inhibitory test of in vivo lipid peroxide

To 0.5 ml of the homogenate obtained above was added 3.5 ml of 0.075M phosphate buffers (pH 7.5) containing sericin L and incubation was continued at 37° C. for 2 hours. The final concentration of sericin L was made to 0.1% or 0.25%. After incubation, 0.5 ml of a sample was recovered and 2.5 ml of ethyl ether/ethanol (1:3, v/v) was added thereto, and then the resulting mixture was vigorously shaken for one minute. Thereafter, the mixture was centrifuged at 1000× g for 5 minutes and the upper layer was measured for absorbance at 234 nm to give an indicator for an antioxidation amount (a conjugated diene). In this Test Example, an antioxidizing ability of sericin was expressed in terms of an inhibitory rate (%) on an increased lipid peroxide.

TABLE 4

| | Inhibitory rate(%) |
|---|---|
| 0.1% Sericin L | 80 |
| 0.25% Sericin L | 86 |

In Test Examples 1~3, TBARS was used as an indicator for a lipid peroxide amount, while a conjugated diene was used as an indicator in Test Example 4. It has been also confirmed from these two different indicators that sericin may possess a potent antioxidizing ability.

TEST EXAMPLE 5

1 ml of 100 mM carbonate buffer (pH 7.4) containing 160 $\mu$M arachidonic acid, 150 $\mu$M $FeCl_3$, 1.0 mM sodium ascorbate and 0.3% sericin was incubated at 37° C. for one hour. After incubation, 2 ml of a mixture of trichloroacetic acid and thiobarbituric acid (containing 15% trichloroacetic acid, 0.375% thiobarbituric acid and 0.25N hydrochloric acid) was added and the mixture was mixed well. Then, 1 ml of 0.1% bovine serum albumin was added and the mixture was heated in a boiling water bath for 15 minutes. After centrifugation, the supernatant was measured for absorbance at 535 nm to determine a TBARS amount. 1,1,3,3-Tetraethoxypropane was used as a standard. In this Test Example, an antioxidizing ability of sericin was similarly expressed as compared with that of the case where no sericin was added.

TABLE 5

| | Inhibitory rate(%) |
|---|---|
| 0.3% Sericin L | 93 |
| 0.3% Sericin H | 95 |

Test Examples 1~4 illustrate the examples using an in vivo constituent system, while Test Example 5 illustrates the example wherein a system composed of a pure chemical compound was used as an experimental system. It has been confirmed that sericin could possess an antioxidizing ability even when such different experimental systems were applied.

It has been suggested from the results of Test Examples 4 and 5 that the presence of an antioxidizing ability of sericin is far more reliable, which does not correspond to the phenomenon observed only in the specific experimental system.

TEST EXAMPLE 6

To $1/15$M phosphate buffer (pH 6.8) containing sericin H or a sericin L were added 0.1 ml of a solution of tyrosinase (derived from mushroom, manufactured by Sigma Chemical Co.) at 0.5 mg/ml ($1/15$M phosphate buffer, pH 6.8) and 0.9 ml of $1/15$M phosphate buffer (pH 6.8) and the mixture was incubated at 25° C. for 10 minutes. Thereafter, 1 ml of 0.3mg/ml DOPA ($1/15$M phosphate buffer, pH 6.8) was added, incubation was performed at 25° C. for 5 minutes and then absorbance at 475 nm (D1) was measured. Separately, a similar procedure was carried out using the enzyme inactivated by heating (D2) to determine an amount of the sericin free DOPA chromium (D3), and then an inhibitory rate was calculated according to the following equation:

Inhibitory rate (%)=((D3−D1)/(D3−D2))×100

As shown in Table 6, it has been confirmed that both of sericin H and sericin L possess an inhibiting ability of tyrosinase activity. In particular, a tyrosinase activity inhibiting ability was ensured to possess at the final concentration of 0.5% or more.

TEST EXAMPLE 7

The same experiment as described in Test Example 6 was repeated except that the final concentration of sericin H and sericin L of 0.5% was applied, and the same experiment as above was also repeated for comparison except that bovine serum albumin (the final concentration of 0.5%) was used. Moreover, a solution of sericin or sericin hydrolyzate dissolved in a phosphate buffer was boiled for 2 hours and then a tyrosinase activity inhibiting ability after heating was also determined.

In comparing tyrosinase activity inhibitory rates between sericin H or sericin L and other common proteins (bovine serum albumin), it has been confirmed that bovine serum albumin does hardly possess a tyrosinase activity inhibiting ability and sericin and sericin hydrolyzate are superior to the albumin.

On the other hand, a tyrosinase activity inhibiting ability of sericin H or sericin L remained substantially unchanged even by heating. Accordingly, it has been confirmed that a tyrosinase activity inhibiting ability of sericin or sericin hydrolyzate is considerably stable to heating.

TABLE 6

| | Tyrosinase activity inhibitory rate(%) | |
|---|---|---|
| Final concentration(%) | Sericin H | Sericin L |
| 0.25 | 6.0 | 5.3 |
| 0.5 | 35.5 | 20.0 |
| 1.0 | 50.0 | 29.1 |

TABLE 7

| | Final concentration(%) | Tyrosinase activity inhibitory rate(%) |
|---|---|---|
| Bovine serum albumin | 0.5 | 5.8 |
| Sericin H (unheated) | 0.5 | 37.5 |
| Sericin H (heated) | 0.5 | 35.0 |
| Sericin L (unheated) | 0.5 | 27.3 |
| Sericin L (heated) | 0.5 | 22.6 |

Sericin is water-soluble and then may be also employed as an antioxidant or a tyrosinase activity inhibitor for the products having a low content of oils and fats. Moreover, it has no promoting effect of lipid peroxide in a low concentration range as seen in vitamin C.

Furthermore, sericin has the characteristics as seen in the protein or peptide derived from natural products, shows a good affinity with the skin, has no accumulating property because of being easily hydrolyzed by a protease and has a high safety, such that it may be utilized for an extensive field including medicines, quasi-drugs, cosmetics, foods, etc. In addition, it has the characteristics that its activity is not inactivated even by heating and it maintains a prolonged inhibiting activity together with safety.

And further, sericin can be easily extracted from an extract of silkworm cocoon or raw silk with a solvent in a high purity as a single protein or peptide and then it becomes available inexpensively, while its aqueous solution is colorless and transparent so that there is no need for stripping and also for complicated treatment steps, which leads to a great advantage.

What is claimed is:

1. A method for the prevention of discoloration or coloration which comprises adding an effective amount of natural sericin to tyrosine and lipid peroxide containing systems to inhibit tyrosinase or lipid peroxide activity.

2. A method for the treatment of human skin which comprises applying a sufficient amount of natural sericin to exert an antioxidizing activity or an inhibiting action on tyrosinase activity.

3. A method of providing an antioxidizing ability or an inhibitory action for tyrosinase activity comprising:
   preparing a composition containing a hydrolyzate of sericin and using the composition to provide the antioxidizing ability or the inhibitory action for tyrosinase activity.

4. A composition useful as an antioxidant or an inhibitor for tyrosinase activity which comprises as an active ingredient a sufficient amount of a hydrolyzate of natural sericin to exert an antioxidizing ability or an inhibitory action on tyrosinase activity.

5. The composition as claimed in claim 1 which is contained in a medicine.

6. The composition as claimed in claim 1 which is contained in a cosmetic.

7. The composition as claimed in claim 1 which is a discoloration inhibitor.

8. The composition as claimed in claim 6 wherein said cosmetic is a bleaching cosmetic.

9. The composition as claimed in claim 1 which is a food additive.

10. The composition as claimed in claim 1 which is contained in a food.

11. The composition as claimed in claim 1 which is contained in a quasi-drug.

12. The composition as claimed in claim 5 wherein said medicine. is a medicine for external use.

13. A composition comprising as an active ingredient a sufficient amount of a hydrolyzate of natural sericin extracted from silkworm cocoon or raw silk to exert an antioxidizing ability or an inhibitory action on tyrosinase activity.

14. A composition comprising a medicinal composition including natural sericin in an amount sufficient to impart to the medicinal composition an antioxidizing ability or an inhibitory action on tyrosinase activity.

15. A composition comprising a food composition including natural sericin in an amount sufficient to impart to the food composition an antioxidizing ability or an inhibitory action on tyrosinase activity.

* * * * *